United States Patent [19]

Hyrman

[11] Patent Number: 4,709,700

[45] Date of Patent: Dec. 1, 1987

[54] ELECTRO CONVULSIVE THERAPY METHOD

[76] Inventor: Vaclav Hyrman, 2420 Norcrest Court, Burnaby, British Columbia, Canada, C3J 1C6

[21] Appl. No.: 710,576

[22] Filed: Mar. 11, 1985

[51] Int. Cl.$^4$ .............................................. A61N 1/36
[52] U.S. Cl. ................................. 128/421; 128/419 S
[58] Field of Search ............... 128/1 C, 419 R, 419 S, 128/421, 791

[56] References Cited

U.S. PATENT DOCUMENTS

| | | | |
|---|---|---|---|
| 2,311,935 | 2/1943 | Dobert | 128/419 S |
| 2,473,378 | 6/1949 | Liberson | 128/419 S |
| 2,558,270 | 6/1951 | Reiter | 128/423 R |
| 2,843,129 | 7/1958 | Oyston | 128/419 S |
| 2,909,178 | 10/1959 | Reiter | 128/419 S |
| 3,850,161 | 11/1974 | Liss | 128/419 S |
| 3,880,170 | 4/1975 | Popov | 128/421 |
| 3,989,051 | 11/1976 | Nozhnikov | 128/421 |

OTHER PUBLICATIONS

Christensen, P. and Koldbaek, I. (1982), EEG Monitored ECT., Brit. J. Psychiat., 141; 19–23.
Fink; M. and Johnson, L.: Monitoring the Duration of Electroconvulsive Therapy Seizures; 'Cuff' and EEG Methods Compared, Arch. Gen. Psychiatry, vol. 39, Oct. 1982:1189–1191.
Friedman, E. et al., (1942) Electrostimulated Convulsive Doses in Intact Humans by Means of Unidirectional Currents, J. Nerv. Ment. Dis. 96, 56–63.
Gordon, D. (1982), Electroconvulsive Therapy with Minimum Hazard, Brit. J. Psychiat. 141; 12–18.
Gordon, D. (1981), The Electrical and Radiological Aspects of ECT, edited by Palmer. R., Oxford Univ. Press, Toronto; 79–96.
Liberson, W. T. (1945), Time Factors in Electric Convulsive Therapy, Yale. J. Biol. Med. 17; 571–578.
Liberson, W. T. (1948), Brief Stimulus Therapy, Physiological and Clinical Observations, Amer. J. Psychiat., vol. 105; 28–39.
Malitz, S. et al. (1982) ECT in the Treatment of Major Affective Disorders, Psych. J. Univ. Ottawa, vol. 7, No. 2; 126–134.
Maletzky, B. M. (1978), Seizure Duration and Clinical Effect in Electroconvulsive Therapy, Comprehens. Psyc., vol. 1, No. 6, 541–550.
Maxwell, R. D. H. (1968), Electrical Factors in Electroconvulsive Therapy, Acta. Psychiat. Scand., 44, 4; 436–448.
Offner, F. (1942), Electrical Properties of Tissues in Shock Therapy, Soc. Expl. Biol. & Med. Proc., vol. 49; 571–575.
Offner, F. (1946), Stimulation with Minimum Power, J. Neurophysiology, vol. 9; 387–390.
Orpin, J. A. (1980), Electroconvulsive Therapy: New Techniques, Psych. J. Univ. Ottawa, vol. V, No. 3; 162–165.
Ottosson; J. O. (1960), Experimental Studies of Memory Impairment after Electroconvulsive Therapy, Acta Psych. Neurol. Scand., Supp. Copenhagen.
Ottosson, J. O. (1961), Electroconvulsive Therapy—electrostimulatory or Convulsive Therapy? J. Neuropsych., vol. 3; 216–220.
Ottosson, J. O. (1961), Seizure Characteristics & Therapeutic Efficiency in Electroconvulsive Therapy, J. Nerv. Ment. Dis., vol. 135; 239–251.
Valentine, M. et al. (1968), A Comparison of Techniques in Electroconvulsive Therapy, Brit. J. Psych., 11; 989–99.

(List continued on next page.)

Primary Examiner—William E. Kamm
Attorney, Agent, or Firm—Carver & Co.

[57] ABSTRACT

A method for electro convulsive therapy comprises placing electrodes on the head of the subject and applying a plurality of short pulses of a unidirectional electric current having a constant peak current. The pulses have a duration of 20–100 microseconds and are delivered at a rate of 100–300 pulses per second.

3 Claims, 8 Drawing Figures

```
PLACE THE
ELECTRODES ON
THE SUBJECTS
HEAD
    │
    ▼
APPLY A PLURALITY OF SHORT PULSES
OF AN ELECTRICAL CURRENT HAVING
CONSTANT PEAK CURRENT. THE
PULSES HAVING A DURATION OF 20-
100 MICROSECONDS AND BEING
DELIVERED AT A RATE OF 125-130
PULSES PER SECOND
```

OTHER PUBLICATIONS

Weaver, L. et al., (1974), Stimulus Parameters in Electroconvulsive Shock, J. Psych. Res., vol. 10; 271-281.

Weaver, L. et al. (1978), The Threshold Number of Pulses in Bilateral and Unilateral ECT, Biol. Psych., vol. 13, No. 2; 227-241.

Weaver, L. et al. (1976), Current Density in Bilateral and Unilateral ECT, Biol. Psych., vol. 11, No. 3; 303-312.

Weaver, L. et al. (1982), Studies in Brief Electroconvulsive Therapy, Biol. Psych., vol. 17, No. 10; 1131-1143.

Woodbury, L. A. et al. (1952), Stimulus Parameters for Electroshock Seizures in Rats, Amer. J. Phys., vol. 170, No. 3; 661-667.

Yudofsky, S. C. (1982), Electroconvulsive Therapy in the Eighties, Amer. J. Psychotherapy, vol. XXXVI, No. 3; 391-398.

PLACE THE ELECTRODES ON THE SUBJECTS HEAD

↓

APPLY A PLURALITY OF SHORT PULSES OF AN ELECTRICAL CURRENT HAVING CONSTANT PEAK CURRENT. THE PULSES HAVING A DURATION OF 20-100 MICROSECONDS AND BEING DELIVERED AT A RATE OF 125-130 PULSES PER SECOND

ELECTRO CONVULSIVE THERAPY METHOD

BACKGROUND OF THE INVENTION

In 1938 Cerletti used modified household current to produce a seizure for therapeutic purposes in the mentally ill. The results were dramatic, and the search for better stimuli began. The optimal stimulus would produce maximum therapeutic benefit with minimal damage. Since the seizure was generally considered to be the therapeutic factor in ECT, currents and waveforms that could produce the seizure with minimal energy were sought.

Within a decade the brief pulse and unilateral ECT techniques were described. Offner (1942) reported that the electric current passing through a living tissue does not quite follow Ohm's law. Later (1946) he postulated that the optimal stimulus would consist of exponentially rising pulses of current, about 1 ms total duration. This waveform proved difficult to produce, and in any event would have reduced the energy required by only 22% relative to move easily generated square pulses. Therefore he endorsed the use of brief square pulses. Liberson (1945) reported his pioneering work with rabbits and guinea pigs, suggested that the best stimulus rate would be between 120 and 150 pulses per second. From clinical experience (1948) he reported that stimuli of less than 0.3 ms pulse duration were unreliable, and those of more than 1 ms required more energy to produce seizures than 1 ms pulses. Friedman and Wilcox (1942) used half sine waves and unidirectional pseudogalvanic waves, inducing seizures with less energy. They also used unilateral electrode placement, resulting in substantially reduced memory impairment. Without anesthesia, however, the patients developed considerable anxiety and strongly resisted treatment, as it took sometimes several seconds before the onset of seizure. The technical limitations of electronics and the exciting psychopharmacological discoveries of the fifties reduced interest in ECT research. Woodbury et al. (1952) published animal research data favoring 50 $\mu$s pulses at rates up to 300 pulses per second. However, in their recommendations for ECT instruments, they chose to disregard their own data, and they endorsed 0.5–1.0 ms pulses at a rate of 120 pulses per second, as they were easier to produce at that time. Possibly these were the reasons why the sine wave and its modifications remained the most popular waveform.

In the sixties, after the routine use of anesthesia and muscle relaxants were introduced, the search for a better stimulus was revived. Evidence was brought forward indicating that the electricity is largely responsible for the memory impairment with ECT, whereas the therapeutic effect depends only upon the seizure itself (Ottosson, 1960, 1961, 1962). Maxwell (1968) summarized the methods of increasing the effeciency of ECT stimulus in seizure induction, relating to the pulse shape, width, rate, voltage and energy. Valentine et al. (1982) studied postictal confusion and made a good case for the brief pulse current and unilateral application of ECT. Weaver et al. (1974, 1978, 1982) established that there is no advantage in exceeding 1 ms pulse width, and that there is no difference in seizure-producing potency of AC and unidirectional stimuli, Orpin (1980) described clinical experience with his own brief pulse instrument. Although he produced seizures with as little as 22 joules (as opposed to 170 joules with sine wave current), he could not demonstrate any clinical advantage. Gordon (1981, 1982) described his brief pulse machine, City University Instrument, using 1 ms stimuli, variable peak current and rate, usually 100 pulses per second. He compared it with various other modern ECT instruments (Orpins, Siemens, Theratronics, Ectron and MECTA) and the comparison favoured his own. Others (Maletzky, 1978, Christensen and Koldbaek, 1982, Malitz et al., 1982, Yudofsky, 1982), consider the MECTA machine, incorporating EEG and ECG recordings, to be the most advanced instrument.

There is no universally accepted standard at present for the specification of dose in ECT. Reasons for this are diverse. While electrical measurements are readily made with simple instrumentation, no single physical parameter has been shown to be a reliable indicator of the clinical dose when other parameters vary. This facility of measurement, however, seems to have encouraged some workers in the field to adopt dosimetry criteria inadequately calibrated with respect to quantifiable clinical effects.

Two very different electrical dosimetry criteria have been proposed in the literature. These shall first be examined for plausibility from a physical point of view. Both will then be shown to be problematic; while each is easily measured, each has important shortcomings which could possibly be overcome.

The first technique, ergometry, measures ECT dose in joules of generated electrical energy applied to electrodes. This is done by multiplying the applied voltage (V) by the current (I) and the duration of the current (t). The energy (W) applied during ECT is given by the simple formula $$W = VIt$$

If practical units are employed (volts, amperes and seconds, respectively, for V, I, and t) the energy, and thus the ergometric dose, will be in joules. With ECT instruments the voltage and the current vary during stimulus application, and a somewhat more difficult technique, called Digital Data Acquisition and Processing (DDAP) is required to measure the ergometric dose according to formula:

$$W = \int V(t) I(t) dt$$

The use of ergometry as the measure of the energy deposited in the brain is unsatisfactory for other reasons too. Skin and skull electrical resistance varies a great deal even in the same individual, depending on such factors as emotions, skin preparation, and electrode placement. The ergometric dose required to deposit a given energy in the brain will vary accordingly.

The second technique, coulometry, determines ECT dose in terms of total charge which flows during the treatment. As Gordon (1981) pointed out, the use of ergometry can be very misleading. He suggests using coulometry instead. This technique is readily applicable by users of constant current instruments. The coulometric dose, Q, is given by the formula:

$$Q = It$$

for steady current, and by the formula:

$$Q = \int I dt$$

for varying current. If practical units are employed, Q will be in coulombs, which are units of electric charge. Moreover, symmetric stimuli, for which the net charge is zero, such as sine waves, do indeed induce convulsions. Gordon (1981) recognized that coulometry was inadequate to specify dose, and he recommended recording and specifying peak current and ergometric dose as well.

More problems are to be encountered by those trying to conceptualize and quantify the electrical energy that may damage the brain. The living brain constantly generates electrical energy (demonstrable by EEG) and absorbs it without any harm. In order to cause any harm, the electrical energy must be deposited in the tissue at a rate which exceeds the capacity of the tissue to absorb it harmlessly. The electrical stimulus may be excessive with respect to energy, time, and space factors involved. The harmful role of energy is probably straightforward—the more energy, the more likely damage will ensue, providing other factors are constant. The role of time is twofold—if the current and tissue volume remain constant, the longer the time, the more likely is the damage. However, if the energy remains constant, the longer time it is applied, the less likely it is to cause damage. For example, 1 W applied to 1 kg of living tissue for 10 days will hardly even raise its temperature, although the energy will be 864,000 J. The same energy applied in 20 minutes with the power of 720 W (the power of a kitchen stove plate) will certainly damage the tissue.

Similarly, the role of space is twofold. The smaller the tissue volume in which a given energy is deposited, the more likely damage will occur (higher energy density). The larger the volume of tissue affected, the more likely the damage will be significant.

Power itself is not a meaningful measure of the dose, as for example 100 V applied for 1 sec. will give the same power, but much smaller dose if applied for 0.1 sec. only.

Evidently energy, power, or charge are not satisfactory single criteria of the electrostimulatory dose, and ECT dosimetry will require further refinement. (Footnote 2.) This issue will be addressed again in the discussion.

SUMMARY OF THE INVENTION

According to the invention, a method for electro convulsive therapy comprises placing electrodes of the head of the subject and applying a plurality of short pulses of a unidirectional electric current having constant peak current. The pulses have a duration of 20–100 microseconds and are delivered at a rate of 100–300 pulses per second.

Preferably, the pulse duration is between 40 and 60 microseconds.

The current rate is preferably 200 pulses per second.

IN THE DRAWINGS

Figures 7, 8:
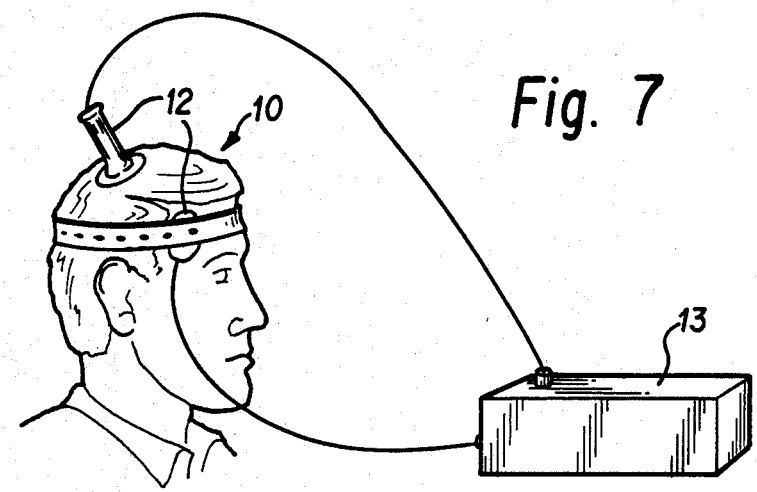
FIG. 7 is a simplified side elevation of a persons's head showing the electrodes attached thereto in a conventional manner.
FIG. 8 is a flow chart illustrating the steps of the method of the present invention.

Referring to FIG. 7 a person's head is generally referred to as 10. Attached to the head by conventional means are electrodes 12 which receive their electrical current from a generator 12.

EXAMPLES

(A) Methods

The search for the perfect stimulus began as an attempt to develop rational guidelines for use in the variety of stimulus settings available on the MECTA instrument. There is no consensus in the literature as to what the physical characteristics of the optimal stimulus should be. It was decided to define the optimal stimulus as a stimulus pattern producing seizures most reliably with the least dose of electrical energy. Bearing in mind the limitations of any single parameter of electrical stimulus as a measure of its potentional to cause tissue damage, the search focused on the density of the energy diposited in the brain over short time (seconds or less) as used in ECT. For that purpose the correct unit of the stimulus energy would be joules per unit of volume of brain tissue, requiring measurements of brain tissue resistance and volume which were not available to us. For the sake of simplicity, coulometry was used in our measurements, as long as the current (0.5 A) and the size of the brain (rabbit) remained constant.

Figure 1:
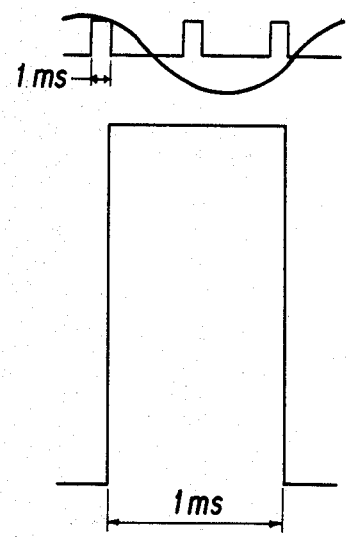
FIG. 1 is a graphical illustration of a square stimulus waveform having a one millisecond unidirectional pulse, the upper portion of the graph showing this waveform patterned at a rate of 200 pulses per second with a 60 Hz sine wave superimposed.

The literature reviewed suggested that the most economical stimulus would likely be a train of unidirectional square pulses, duration about 1.0 ms each, rate about 200 pulses per second, and constant peak current about 1.1 A. (FIG. 1)

The experimental ECT machine was at first designed to provide unidirection 1 ms brief pulse stimuli, constant peak current 0.5 A, rates 2 pulses per second to 300 pulses per second, and to deliver a preset number of pulses. Later it was rebuilt twice, to test specific hypotheses described below.

Thirteen medium to large size domestic rabbits of various breeds and one pig were the research subjects and they received altogether over 450 shocks. Rabbits were chosen as experimental animals because some of the original work in ECT was done with rabbits and rabbits were easily available. The pig was chosen as an animal whose head size resembled human, in preparation for clinical application.

Figure 3:
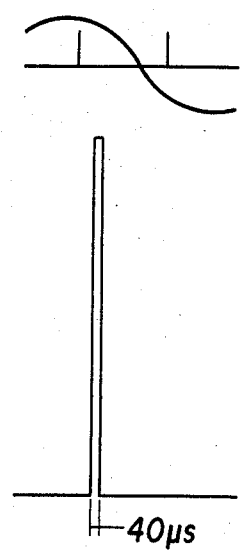
FIG. 3 is a graphical representation similar to FIG. 1 in FIG. 2 showing a single 40 microsecond pulse.

The electric stimuli consisted of trains of nearly square pulses (the peak current for each pulse was reached in less than 2 μs, maintained for the pulse duration, and declined again in less than 2 μs). The stimulus characteristics were recorded in terms of rate (r), current (l), pulse width or duration (P) and number of pulses per stimulus (N). Part of the investigation involved use of 1 ms pulses interrupted 1 to 4 times, creating thus groups of 1 to 5 very brief pulses (FIG. 3). These pulses within a pulse will be called "micropulses", and described in terms of rate of the groups (r), current (I), micropulse width or duration (M), number of micropulse groups or pulses per stimulus (N), and number of micropulses per 1 ms group (n).

The stimuli were delivered using round convex steel electrodes of 18 mm diameter, attached bitemporally by an elastic harness to the animal's head. The hair in the area corresponding to the placement of the electrodes was removed using a commercial depilatory cream, and a standard conductive electrode jelly was applied on the skin to increase conductivity. The interelectrode resistance was measured prior to each stimulus using 1.5 V ohmmeter, and found to vary widely from 100 to 4,000 Ohms. The seizure thresholds were determined in 3 to 7 rabbits for each point on the graphs. The points on the graphs represent mean values of all measurements. In all the experiments with rabbits reported here the peak current was constant 0.5 A, and the coulometric dose (Q) was calculated using the formula:

$$Q = NIP$$

and in the case of micropulses, formula:

$$Q = NnIM$$

The duration of stimulation (d) varied widely between 26 ms and 11 s depending on the stimulus pattern pattern used, and usually was not recorded, as it could be easily calculated using the formula:

$$d = N/(r)$$

Measurement of voltage between electrodes was done on a dead rabbit only, yielding values in the range of 30–90 V, changing inconsistently even during single stimulus application. The current pattern was registered using a storage oscilloscope, in order to eliminate false results due to circuitry malfunctions. Twice the experiments of several days were repeated in reverse order, on order to avoid possible effect of previous shocks on seizure threshold. No such effect of any significance would be found.

Audio recordings were made of all the experiments. Data from these recordings included comments about the quality of seizure response, the onset and the termination of the seizure. The duration of seizures was then determined from the audio recordings using a stopwatch, and added to the data base. A stimulus was considered to be above threshold if immediately after the stimulus application the response began with a tonic seizure of several seconds duration, and proceeded into a clonic convulsion.

The statistical evaluation of the experimental data was done laboriously, using the MAXISTAT statistical package (Walonick, 1981) on TRS-80 microcomputer. Unless stated otherwise, the results reported tested beyond the 0.005 significance level.

Hypotheses and research questions were formulated as new experimental data emerged, and they presented together with the results in chronological order as they occurred.

(B) Results

Figure 4:
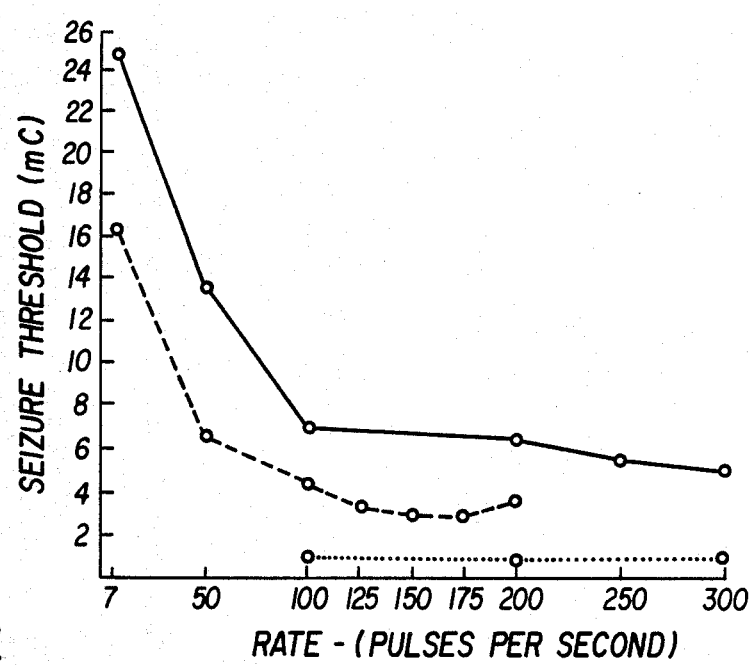
FIG. 4 is a graph plotting seizure threshold in millicoulombs against current rate in pulses per second.

1. The effect of stimulus rate on seizure threshold: Seizure thresholds for various rates using 1 ms pulses were determined, and the low rates were found to be quite ineffective. The lower the rate, the more energy was required to produce a seizure (FIG. 4, full line). The optimal rate appears to be in the range of 125 to 300 pulses per second (difference among thresholds in this range did not reach statistical significance).

Figure 2:
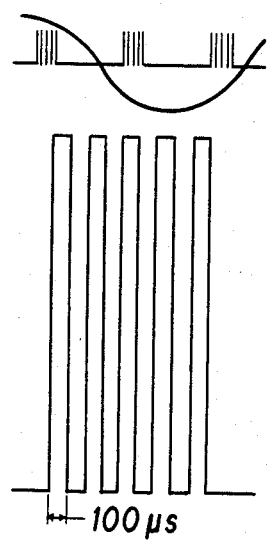
FIG. 2 is a graphical representation similar to FIG. 1 showing five 100 microsecond micropulses in a one millisecond pulse.

2. The effect of dividing 1 ms pulses in five 100 $\mu$s "micropulses" (FIG. 2): this stimulus pattern was almost as effective as the full pulses, while depositing only half the energy (FIG. 4, interrupted line).

Figure 5:
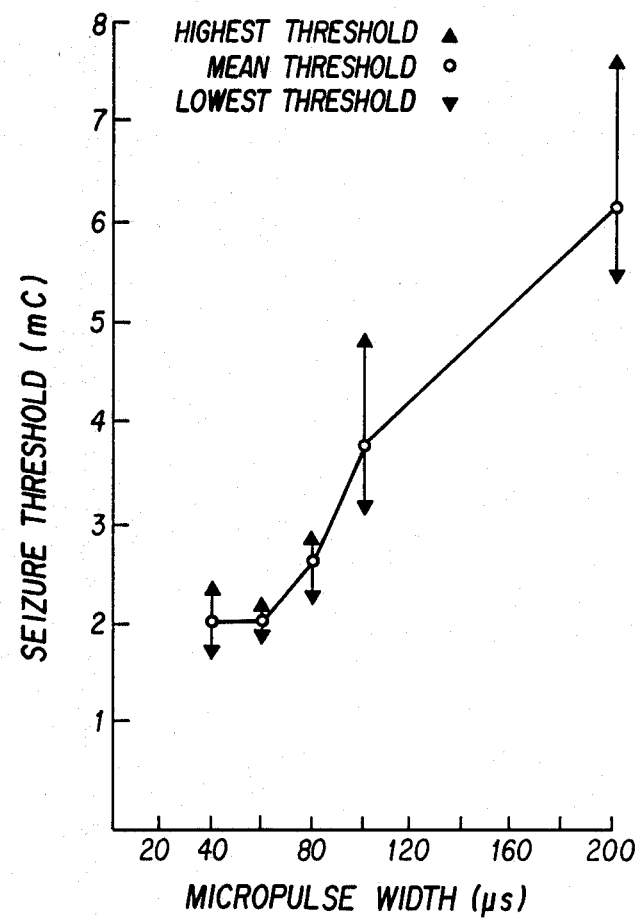
FIG. 5 is a graph plotting seizure threshold in millicoulombs against micropulse width in microseconds.

3. The effect of "micropulse" width on the stimulus efficiency (efficiency in this context means capability of the stimulus to produce seizures with the lowest coulometric dose): Micropulses shorter than 100 $\mu$s were more efficient than 100 $\mu$s micropulses (FIG. 5). There seemed to be a limit to the increase of the efficiency somewhere between 40 and 60 $\mu$s.

Figure 6:
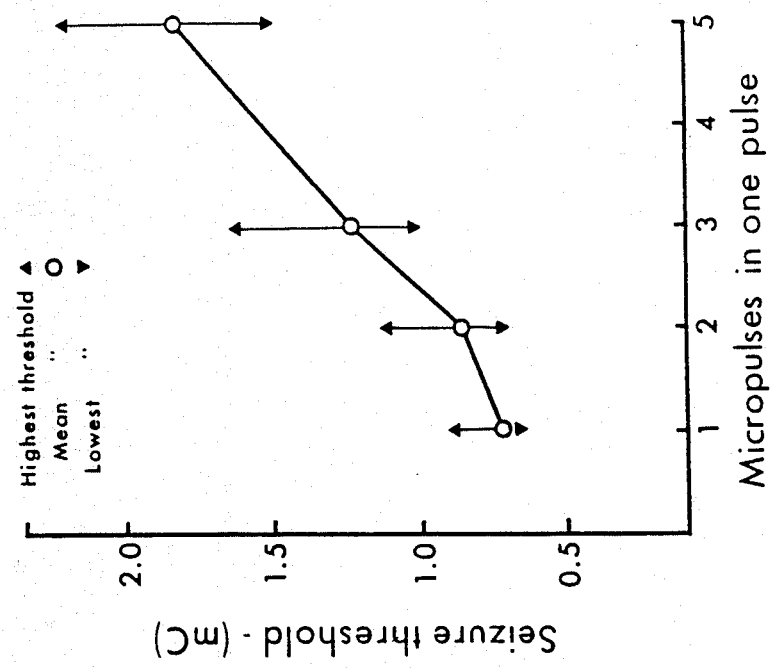
FIG. 6 is a graph plotting seizure threshold in millicoulombs against the number of micropulses in one pulse.

4. The effect of the number of micropulses in the 1 ms group on stimulus efficiency: In comparison to five micropulses in a group, three were more effective, two were even better, and one was the best (FIG. 6). Thus there appears to be no advantage in using volleys of micropulses, and very brief (40–60 $\mu$s pulses of frequency 200 Hz) are the most efficient stimulus pattern.

5. The effect of stimulus rate on the efficiency of 40 $\mu$s pulses: Thresholds for rates 100, 200 and 300 pulses per second (FIG. 4, dotted line) were determined, and 200 pulses per second was found to be the most effective (the differences were not significant statistically).

6. Inter-species transferability of the results of these experiments: A pig was chosen as the next subject, and the stimulus parameters were estimated to achieve similar stimulus energy density as for the threshold stimuli in rabbits. The interelectrode distance in the rabbit was approximately 30 mm, whereas in the pig it was 130 mm. With a constant current instrument (assuming the brain is roughly cubical), the deposited energy density is inversely related to the square of interelectrode distance, and directly related to time and the square of intensity. With 40 $\mu$s pulses at rate 200 pulses per second and current 0.5 A, the average rabbits seizure threshold was 38 pulses. Using the same peak current (0.5 A) and disregarding the anatomical differences between species, the pig would require more than 700 pulses in order to reach the same energy density. This would take almost 4 seconds, which may be impractical. Setting the peak current to maximum (1.4 A), 73 pulses of b 50 $\mu$s width was calculated to achieve the same energy density in approximately 0.3 seconds. These calculations were done using the formula:

$$NPI^2/D^2 = N_l P_l I_l^2 / D_l^2$$

where D is the distance between electrodes and the subscript "1" indicates stimulus parameters for the first animal, rabbit. This extrapolation is, or course, susceptible to error because of anatomical differences both between species and between individuals.

The seizure threshold for the pig was thus estimated at 73 pulses of 50 $\mu$s pulse width, rate 200 pulses per second, and peak intensity 1.4 A. 80 pulses produced a seizure, 50 pulses failed to produce a seizure, and on restimulation with 90 pulses a seizure was produced again. The close correspondence of predicted threshold and experimental results supports the notion that the animal data could be extrapolated to humans with a fair degree of accuracy.

OTHER OBSERVATIONS

Stimuli below the threshold produced only startle response, threshold stimuli produced incomplete seizures, partial seizures or delayed seizures. Stimuli above the threshold produced immediate and complete seizure response. Stimuli that were way above the threshold produced especially prolonged and vigorous seizures. The pulse width had no bearing on seizure duration whatsoever. Although the resistance varied a great deal, there was no correlation between the resistance and the coulometric dose required to produce seizures. At rates above 100 pulses per second the seizure thresholds of individual animals remained remarkably constant, within 25% of the coulometric dose. Even the interindividual variations in seizure threshold were relatively small, i.e. the highest threshold was less than twice the lowest one, as long as other stimulus characteristics remained constant.

(C) Discussion

The clinical application of these findings is so far limited. For the clinician using the MECTA instrument and wishing to use minimal energy to produce seizures, the data presented suggest that the stimulus rate should be set at maximum (70 pulses per second), time at maximum (2 s), and only the pulse width should be varied depending on the patient's response. In our experience using unilateral temporo-parietal position of electrodes, all patients will convulse adequately using the pulse width 0.5 ms, and some require less. This setting delivers one third of the energy the instrument is designed to deliver at maximum setting, and it is less than what we routinely used before. Clinically, no difference in terms of side effects or therapeutic efficacy using this technique has been observed.

Theoretical implications for future research and clinical use of ECT may be much farther reaching. The experiments did not address the question of relative importance of the constant current versus number of pulses setting. There may well be an optimum number of pulses, in which case only the current should be set, and vice versa. In future research it will be desirable to find seizure thresholds for various stimulus currents and to plot the energy used against both the stimulus current and the number of pulses (time) used. As mentioned above, the choice of an adequate measure of electrostimulatory dose presents a difficult theoretical problem. For the purpose of the study presented above millicoulombs (mC) were selected as the most suitable measure of energy used, as long as the stimulus current, head size and electrode placement remained constant. When the head size and interelectrode distance (D) were changed, dividing the energy by the square of interelectrode distance proved to be a suitable way of scaling the stimulus energy density, and the formula:

$$ESD = \int I(t)^2 dt/d^2$$

to express the electrostimulatory dose (ESD) was adequate. This formula could not be used to compare the doses in ECT when the electrode placement varies. Weaver et al. (1976) discussed in detail how vastly different the energy density distribution in the brain is in unilateral and bilateral ECT. Clinically, a meaningful way of specifying the electrostimulatory dose (ESD) would be ESD units corresponding to the density of the energy deposited in the brain during ECT. As long as the electrode placement remained constant, they could be calculated according to the first part of the formula, i.e.:

$$ESD = \int I(t)^2 dt$$

This study went well beyond the scope of its original purpose, i.e. to develop rational guidelines for using the MECTA instrument. As a result of this exploration, it is now possible to define a stimulus pattern capable of producing seizures reliably with less than 15% of the energy required by the advance brief pulse instruments (such as MECTA), or less than 6% of the energy used by the sine wave instruments.

Pulses of duration between 40 and 50 $\mu$s at rate around 200 pulses per second, were found to be reliable and more efficient than the traditional stimulus patterns for seizure induction.

Although the experiments were done with rabbits, the results should be easily adaptable to humans, with the only major modification being the constant current limitation setting. Our experiments with a pig indicate, that his seizure threshold could be predicted with reasonable accuracy.

(D) Footnotes

Footnote 1: DDAP is the name given to the class of data logging and control techniques which provide real time and rapid access to results of preprogrammed data reduction algorithms. DDAP is used increasingly in instrumentation, for example in process control in paper mills. In that application a radiation thickness monitor can be made to read directly in thickness while taking account of correction necessary due to varying temperature and moisture content. This is accomplished by feeding the data from three different sensors into one central processor, typically a microcomputer. A version of DDAP is used to control the spark timing in many modern automobiles. In ECT real-time appropriate parameters with sensors digitizing the outputs, and processing these outputs with appropriate algorithm. The result of this calculation could even be fed back to regulate the dose output automatically.

Footnote 2: There are, perhaps, important lessons to be learned from another discipline, radiology. There, too, dosimetry was slow to evolve. Initially clinical dosimetry was calibrated to the "erythema dose" unit. A radiologist learned by experience how long an arm, for example had to be irradiated to produce an x-ray picture compared to the length of time required to noticeably redden fthe skin of the arm. This method was both instrument and patient dependent. Time, alone could not be used since the output of older x-ray machines varied over long times. Interestingly, the rays responsible for producing the dosimetry were extraneous for radiographic purposes. Currently they are considered potentially harmful and are filtered from the output of x-ray machines. A fundamentally electrical unit the roentgen, replaced the erythema dose. This, too was found to be flawed because it was defined in terms of coulometry of ions in dry air, and it did not correspond well to what happens in living tissues. The roentgen was replaced by an ergometric unit, the rad, which was picked to have a value (100 ergs per gram) close to that of the roentgen in dry air (94 ergs per gram). This unit, while objective and easily measured, was found unsuitable for clinical extension to dosimetry of other forms of ionizing radiation. The rad was replaced, therefore, by the rem, which included consideration of the relative biological effectiveness (rbe) of the particular type of radiation. Neutrons are considered to be an order of magnitude higher in rbe than are x-rays, so the distinction is not just fine tuning. Currently many different forms of ionizing radiation are in use for therapy and diagnostic procedures. These range from ordinary UV radiation to particles as exotic as positrons and pi mesons. Calibration of relative clinical efficacy and development of corresponding appropriate dosimetry is still at the stage of frontier research in, for example, cancer therapy. The parallel between radiology and ECT is that neither ergometry nor coulometry can serve aedquately in their simplest forms. Like the soft x-rays which cause erythema, harmful components of ECT should be identified and minimized, and they should not become important dosimetric factors.

Footnote 3: A study to elucidate the importance of current setting and to compare unidirectional and alternating pulses is now under way. The preliminary results indicate that the most efficient peak current setting of unidirectional 50 $\mu$s pulses of 200 pulses per second rate is in rabbits between 0.2 and 0.3 A. Calculations suggest that the optimal peak current for bi-temporal electrode application in humans will be between 0.7–1.4 A, similarly to the currents used in contemporary brief pulse instruments.

I claim:

1. A method for electro convulsive therapy comprising placing electrodes on the head of a subject and applying a plurality of short pulses of an electric current, said pulses having a duration of 20–100 microseconds and being delivered at a rate of 125 to 300 pulses per second.

2. A method as claimed in claim 1 wherein the rate is generally 200 pulses per second.

3. A method as claimed in claim 1, wherein the pulse duration is between 40 and 60 microseconds.

* * * * *

UNITED STATES PATENT AND TRADEMARK OFFICE
CERTIFICATE OF CORRECTION

PATENT NO. : 4,709,700

DATED : December 1, 1987

INVENTOR(S) : Vaclav Hyrman

It is certified that error appears in the above-identified patent and that said Letters Patent is hereby corrected as shown below:

Figure 8 should be deleted to appear as shown on the attached sheet.

Signed and Sealed this

Twenty-sixth Day of July, 1988

Attest:

DONALD J. QUIGG

*Attesting Officer*     *Commissioner of Patents and Trademarks*

UNITED STATES PATENT AND TRADEMARK OFFICE
CERTIFICATE OF CORRECTION

PATENT NO. :   4,709,700                              Page 2 of 2

DATED      :   December 1, 1987

INVENTOR(S):   Vaclav Hyrman

It is certified that error appears in the above-identified patent and that said Letters Patent is hereby corrected as shown below:

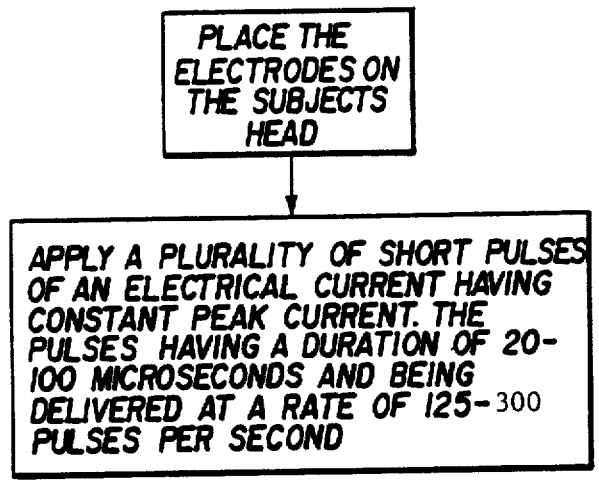

Fig. 8